United States Patent [19]
Mälkki et al.

[11] Patent Number: 5,846,590
[45] Date of Patent: Dec. 8, 1998

[54] METHOD FOR ENRICHING SOLUBLE DIETARY FIBRE

[75] Inventors: Yrjö Mälkki; Olavi Myllymäki, both of Espoo, Finland

[73] Assignee: Exavena OY, Espoo, Finland

[21] Appl. No.: 564,336

[22] PCT Filed: May 27, 1994

[86] PCT No.: PCT/FI94/00212

§ 371 Date: Dec. 4, 1995

§ 102(e) Date: Dec. 4, 1995

[87] PCT Pub. No.: WO94/28742

PCT Pub. Date: Dec. 22, 1994

[30] Foreign Application Priority Data

Jun. 4, 1993 [FI] Finland .................................. 932558

[51] Int. Cl.⁶ .............................. A23L 1/10; A23L 1/308; A23B 4/03
[52] U.S. Cl. .................... 426/443; 426/615; 426/452; 426/456; 426/459; 426/463; 426/469; 426/482
[58] Field of Search ................................ 426/615, 443, 426/452, 456, 459, 463, 469, 482

[56] References Cited

U.S. PATENT DOCUMENTS

| | | | |
|---|---|---|---|
| 4,804,545 | 2/1989 | Goering et al. | 426/28 |
| 5,106,640 | 4/1992 | Lehtomäki et al. | 426/436 |
| 5,169,660 | 12/1992 | Collins et al. | 426/271 |

FOREIGN PATENT DOCUMENTS

PCT/FI88/ 00125 8/1988 Finland .

OTHER PUBLICATIONS

Wood, P. J. Weisz, J and Fedec, P. (1991) Potential for B–glucan enrichment in brand derived from oat . . . Cereal Chemistry 68, 48.

Auti., K., Myllymaki, O., Suortti, T. Saastamoninen, M. and Poutanen K. (1992) Physical Properties of . . . Food Hydrocolloids 5, 513–522.

*Primary Examiner*—Lila Feisee
*Assistant Examiner*—Geetha P. Bansal
*Attorney, Agent, or Firm*—Fulbright & Jaworski L.L.P.

[57] ABSTRACT

The subject of this invention is a method for producing a product with an enriched content of soluble dietary fiber, such as β-glucan and/or pentosans from a raw material deriving from cereal grains, by using thermal, enzymatic or osmotic treatments or combinations of these. As a first step, suspending of milled cereal or a fraction of cereal in water and when needed, a limited proteolysis is performed in order to improve the solubility of the fiber. Temperature of the mixture is elevated, and the soluble fiber is precipitated with a polar organic solvent on solid carrier particles, which can derive from the raw material or are added in the suspension. A fine fraction, consisting primarily of starch, is separated from the more coarse fraction containing the precipitated fiber, by using methods based on the particle size or density. When processing materials rich in fat, the soluble fiber fraction is extracted with a concentrated polar organic solvent for removing the residual lipids, and the particles obtained are finally dried.

19 Claims, No Drawings

METHOD FOR ENRICHING SOLUBLE DIETARY FIBRE

The subject of this invention is a method for preparing concentrates of soluble dietary fibre, such as β-glucan, and/or pentosans, from a raw material deriving from cereal grains. In particular, according to the invention, preparations rich in β-glucan, which expression is used for β- (1→3) (1→4) D-glucan, or pentosans, are made from grains of oat, barley or rye, which preparations dissolve rapidly in water and elevate the viscosity of the solutions and act as water binding agents in the digestive tract or in food preparations.

β-Glucan acts in the human digestive tract as a soluble fibre component and functions in particular as a reducer of the cholesterol content of blood, and by attenuating fluctuations in postprandial blood glucose concentration. Both of these effects are based on the increase of viscosity in the contents of the stomach and intestines. In addition, the viscosity elevating and binding properties of β-glucan can potentially be exploited in several technological applications.

β-Glucan has been found plentifully in grains of barley, oats and rye. Preparation of pure or nearly pure β-glucan from cereal grains in laboratory scale is known from several patent and scientific publications, and has been reviewed e.g. in the Finnish patent No. 84775 and conforming European patent application No 379499 of the inventors of the present invention. Methods for preparing products with an enriched content of β-glucan have been reviewed by Paton and Lenz in 1993 in the book Oat Bran, published by the American Association of Cereal Chemists. There exist also several barley cultivar varieties where the content of β-glucan is already in the grains as high as in the oat bran concentrates, that is from 14 to 17%.

A difficulty in the use of both pure or nearly pure isolated β-glucan, of preparations enriched in the content of β-glucan, and of barley rich in β-glucan, is the slow, incomplete, and not easily controllable solubility of β-glucan. A rapid dissolving and elevation of viscosity are important, among others, when physiological effects are the goal. In some of them, a solubility during less than 15 minutes is necessary. Of β-glucan present in the grains, usually less than a half is soluble in hot water. A weak solubility results partly from the molecular weight distribution, only the fractions with a lower molecular weight being water soluble. In addition, in β-glucan of both of barley (Forrest and Wainwright, Journal of the Institute of Brewing 83 (1977) pp. 279–286) and of oat (Vaum and Smidsrød, Carbohydrate Polymers 9 (1988) pp. 103–117), there has been found tightly bound protein or peptide, which presumably binds molecules to the cell wall and probably also to each other thus elevating the apparent molecular weight. The solubility is retarded both by other components of the grain, which limit the diffusion of water, and by the vigorous caking tendency of β-glucan when connected with water.

The solubility is increasing and speeded up during processing, effected both by heat and mechanical forces and by β-glucanase or pentosanase enzymes. Viscosity elevating properties are, however, simultaneously reduced to an extent, where the physiologically advantageous effects and the possibilities for technological applications are substantially reduced or totally lost. For example, the part of barley β-glucan which can be rendered water soluble has usually a molecular size of a half or one third of that in oat soluble β-glucan, and its viscosity properties are correspondingly weaker. The ubiquitous presence of β-glucanases in many food raw materials and as produced by several microbial species, and the high heat resistance of these enzymes, form also an uncertainty factor for preserving β-glucan in water-containing foods. Consequently, a reproducible dosage can be achieved only by using dry preparations, but the solubility of the present preparations is too slow and incomplete for achieving an effective action.

The main component of the soluble dietary.. fibre in rye are pentosans, and in addition β-glucan occurs. Technologically the so far most important interest in these pentosans is in the bakery industry, due to their water-binding ability, which improves the preservation of freshness in bread. Medical effect have the dietary fibre of rye and the polyphenolic compounds following it, which act by preventing cancers, especially breast and colon cancer.

The difficulty in the preventive use of dietary fibre from all of these cereal grains is the low content of the effective components in the cereal grains, which has created efforts for their concentration.

A method for enzymatic modification of β-glucan containing materials has been presented by Inglett in the U.S. Pat. Nos. 4,996,063 and 5,082,673. In these methods, starch is hydrolyzed to maltodextrin by α-amylase, whereby also β-glucan is downgraded to such an extent that it is not to be expected to have any physiological effects. In a method published by Wilhelm and coworkers (Stärke 41 (1989) pp. 372–376), oat raw material is treated by cellulolytic enzymes to separate starch and protein. The content of β-glucan of the products obtained is not given, but it is probable, that a technical cellulolytic enzyme preparation always has also activity for breaking down β-glucan, and thus the content of viscosity elevating β-glucan in the fractions is probably small.

Enzymatic solubilization of barley β-glucan has been studied by Yin and collaborators (Journal of the Institute of Brewing 95 (1989) pp. 195–198). This group has found that several mold species present on barley grains can form enzymes solubilizing β-glucan. These enzymes have, however, reduced the viscosity, and thus they cannot be exploited for making high-viscous β-glucan preparations.

Forrest and Wainwright have in their publication cited above studied also the effect of proteolytic enzymes on the molecular weight and viscosity of barley β-glucan. The experiments showed a lowering of both the molecular weight and viscosity, thermolysin having the highest effect, papain, chymotrypsin and trypsin a weaker effect. Malkki and associates (Cereal Chemistry 69 (1992) pp. 647–653) found that trypsin decreases the viscosity of oat β-glucan, and Autio and associates (Food Hydrocolloids 5 (1992) pp. 513–522) found this effect being of different magnitude with different cultivar varieties of oats. Because no β-glucanase activity was detected in trypsin, the lowering of viscosity has evidently been caused by breaking down the bonds formed by a protein or peptide between the β-glucan molecules.

In a further study on the properties of oat cultivar varieties it has been now surprisingly found, that a mild treatment with a proteolytic enzyme leads, contrary to previously published observations, to an elevation of viscosity of β-glucan of certain varieties. This effect has been accentuated by subsequent thermal, solvent and mechanical treatments. In this connection it has further been observed, that an enrichment of dietary fibre and the elevation of its viscosity properties can also be achieved by a thermal and subsequent solvent treatment without a previous enzyme treatment. On the basis of these observations, a process was developed for enriching dietary fibre and for producing rapidly soluble concentrates of β-glucan and pentosans.

Essential characteristics of the method are presented in the claims attached.

In the process according to the invention, grains of cereals containing soluble dietary fibre, such as oat, barley or rye or fractions separated from these, can be used as a raw material. As a pretreatment of the raw material, it is dehulled, ground and the β-glucanase and pentosanase activities are inactivated, unless this has not been effected in the preceding treatments. The pre-treated finely ground material is suspended in water using preferably an amount of water which is smaller than that needed to gelatinize the starch in the raw material at temperatures under 100° C. Suspending can be started at ambient temperature by adding in water of for instance 20° C. the raw material, which starts to absorb water and causes the swelling of the raw material. For species and cultivar varieties, for which a proteolytic treatment is needed to improve the solubility and viscosity of the fibre, it is performed at this step, at the optimal pH value and temperature of the enzyme. The temperature of the mixture is elevated to 60°–85° C., by continuing simultaneously the imbibition of water in the raw material and extracting the soluble fibre at these higher temperatures. To the hot suspension, polar organic solvent selected preferably from the group of aliphatic $C_1$ to $C_6$ alcohols and acetone, is added in an amount 80 to 140% of the weight of the suspension, to precipitate the soluble fibre on insoluble carrier particles, which can derive from the cereal raw material or be added in the suspension obtained from the raw material. As an added material, cellulose or diatomaceous earth, for instance, can be used. The suspension is homogenized by using impact and shearing actions, by treating the suspension for instance with a blade mixer or in a colloid mill, and the solid material is concentrated in respect of soluble fibre using operations based on the particle size and density, such as sedimenting, wet sieving, centrifuging or by hydrocyclones, whereby a part of the starch can be separated as a fine-granuled fraction. The solid factions are dried, whereby the main part of the solvent absorbed can be recovered. Alternatively or in addition, the concentration of the solid material in respect of the soluble fibre can be performed after the drying by operations such as sieving or air classification. When materials rich in fats are processed, the residual fat content can be extracted by a concentrated polar solvent before drying. Strongly polar lipids can be recovered from the solvent-water mixture obtained after the precipitation step, the less polar and non-polar lipids from the extract obtained with the said concentrated organic solvent. The solvents can be recirculated.

When using proteolysis at the hydratation stage, an enzyme has to be selected which does not have at the pH range used during the process any considerable β-glucanase or pentosanase activity. As an example of suitable enzymes, trypsin can be mentioned. The objective of the proteolytic stage is to separate β-glucan from the cell wall and to break down protein and peptide bonds between the molecular chains of β-glucan, and thus to improve the solubility and viscosity properties. However, continuing the proteolysis after an optimal stage leads to a reduction of the viscosity, which has been the reason for the observations made in the previous studies on the effect of proteolysis on β-glucan or materials containing it. Since even within the same cereal plant species, the content of β-glucan, its location in the grain, its viscosity properties, and its sensitivity towards proteolysis vary among the cultivar varieties, as it is known from the previous literature, the dosage and the treatment time have to be determined separately for each cereal species and cultivar variety, and for each enzyme.

β-Glucanase activity or side activity is rather common among enzymes prepared with the aid of microbial species. For this reason the selection of enzyme should be made from sources known not to contain β-glucanase activity at the pH desired, or from preparations purified or inactivated from that activity.

The purpose of the thermal treatment after the proteolytic stage is on one hand an imbibition of water into the raw material at a high temperature, to separate β-glucan and pentosans from the other components of the cell wall, on the other to inactivate the protease, as completely as possible. In the selection of the temperature and time combination and the amount of added water in the thermal treatment, the limiting factor is to avoid an extensive gelatinization of the starch. As guidelines for the conditions can be regarded those combinations, at which the birefringence of the starch granules can be lost, but the granules as observed microscopically remain intact. Due to this limit, a complete inactivation of the most thermotolerant proteases is not possible.

Under the stages of imbibition of water and heating, there occurs a swelling of the tissues and their parts containing soluble fibre, but a more intensive disintegration of starch granules starts at first after reaching the gelatinization temperature. The hydratation of starch can be limited except by the temperature also by limiting the amount of water present and mechanical damages of the granules. Thus mixing, mass and heat transfer operations before the precipitation stage have to be performed by using weak shearing forces.

A precipitation of the fibre in the presence of an insoluble carrier causes a part of β-glucan to precipitate on the surface of solid particles, and thus a greater effective surface of the soluble fibre is achieved. This affects advantageously the redissolving properties.

The changes in volume at the swelling as well as at the precipitation stages are greater in the tissues and particles containing soluble fibre, as compared to starch granules and insoluble fibre containing tissues. It is probable that in the process described, other separation effects but those caused by proteolytic enzyme are for a great part caused by these changes in volume.

The method and properties of the products are described in the following examples. Examples 1 to 3 describe effets of trypsin on the viscosity properties, and Examples 3 to 6 the method according to the invention.

EXAMPLE 1

From oat varieties Sang, cultivated in Sweden, and Yty, cultivated in Finland, fibre concentrates were prepared by separating the bran by dry milling, by removing the fat with ethanol extraction, and by separating starch by air sieving after fine grinding. β-Glucan content of these concentrates were 20.8% for the variety Sang, and 26.1% for the variety Yty, respectively.

To verify the viscosity properties, 2.5 g of the concentrates were suspended in 95 ml of sodium phosphate buffer, pH 2.5. This gave a calculated concentration of β-glucan of 0.505% for the variety Sang, and 0.67% for the variety Yty, in the suspension. The suspensions were incubated by shaking at 37° C., thus simulating conditions in stomach. The same concentrates were also extracted in a pH 7.0 buffer in the presence of 0.63 g/L trypsin, the activity of which was 2000 EU/g. Viscosities of the suspensions were measured by using a Bohlin-visco 88 rheometer at 32° C. and at several shear rates. This equipment does not allow low viscosities to be measured at low shear rates. Results were as follows (n.m.=not measurable):

| Variety | pH | Trypsin | Extraction time, h | Viscosity, mPa s | |
|---------|-----|---------|------|---------------------|-----|
| | | | | 77 s$^{-1}$ | 697 s$^{-1}$ |
| Yty | 2.5 | − | 0.5 | n.m. | 24 |
| | 2.5 | − | 1.0 | n.m. | 32 |
| | 2.5 | − | 1.5 | 110 | 34 |
| | 2.5 | − | 2.0 | 129 | 30 |
| Sang | 2.5 | − | 0.5 | n.m. | 15 |
| | 2.5 | − | 1.0 | n.m. | 17 |
| | 2.5 | − | 1.5 | n.m. | 18 |
| | 2.5 | − | 2.0 | n.m. | 19 |
| Yty | 7.5 | + | 1.0 | 156 | 45 |
| | 7.5 | + | 2.0 | 205 | 58 |
| Sang | 7.5 | + | 1.0 | n.m. | 22 |
| | 7.5 | + | 2.0 | n.m. | 29 |

EXAMPLE 2

40 g of concentrates prepared as described in Example 1 from the varieties Sang and Yty were suspended in 200 g of phosphate buffer pH 7, and incubated overnight at 40° C. with varying amounts of trypsin. To the mixture which now had a pasty consistency, 400 ml of ethanol was added, the precipitate was separated by filtration, washed with a small amount of ethanol, and dried. Samples of fibre preparations were suspended in phosphate buffer of pH 2.5, at a concentration of 2.5 g/95 ml, incubated as in the Example 1, and the viscosities were determined as in Example 1, at 32° C. Following results indicate a need to limit the trypsin treatment to an optimal level:

| Trypsin g/L | Extraction time, min | Viscosity mPa · s | | | |
|---|---|---|---|---|---|
| | | 24 s$^{-1}$ | 697 s$^{-1}$ | 697 s$^{-1}$ | 697 s$^{-1}$ |
| | | Yty, test 1 | | Yty, test 2 | Sang |
| 0 | 10 | n.m. | 43 | | |
| 0.25 | 10 | 285 | 64 | 61 | 26 |
| | 20 | | | 66 | 31 |
| | 30 | 441 | 76 | | |
| | 60 | 471 | 80 | | |
| | 120 | 528 | 86 | | |
| 0.5 | 10 | n.m. | 60 | 48 | 35 |
| | 20 | | | 57 | 37 |
| | 30 | | | 60 | 39 |
| 1.0 | 10 | n.m. | 44 | | |
| 2.0 | 10 | n.m. | 39 | | |

EXAMPLE 3

Fibre concentrate prepared as described in the first paragraph of Example 1 from the variety Yty, was incubated in the presence of various amounts of trypsin at 40° C. in sodium phosphate buffer of pH 7.5, during 2 hours. After the treatment, the temperature of the suspension was elevated to 0° C. and the incubation was continued at this temperature for one hour. Subsequently, 94% ethanol was added in an amount being 133% of the weight of the suspension, the mixture was homogenized by a shearing homogenizer, the solids separated and dried. The yield of the dry preparation was 90% of the starting material, and the β-glucan content of the samples, as determined with an analysator based on the colour of calcofluor, varied between 27.5 and 30.5%, whereas the content in the starting material as determined by the same method was 16.5%, and according to the enzymatic method 26.1%. The elevated content of β-glucan according to the calcofluor method indicates an increase in the share of the soluble β-glucan. Of the dry preparations obtained, suspensions in sodium phosphate buffer of pH 2.5 in the concentrations given in Examples 1 and 2 were made. Suspensions were extracted at 37° C. Viscosity was measured as in Examples 1 and 2, at 32° C. Results of the measurements were as follows:

| Trypsin g/L | Extraction time, min | Viscosity, mPa · s | |
|---|---|---|---|
| | | 43 s$^{-1}$ | 697 s$^{-1}$ |
| 0.25 | 10 | 242 | 63 |
| | 20 | 335 | 73 |
| | 30 | 367 | 77 |
| 1.0 | 10 | 348 | 74 |
| | 20 | 440 | 86 |
| | 30 | 472 | 89 |
| 2.0 | 10 | 414 | 85 |
| | 20 | 498 | 92 |
| | 30 | 501 | 93 |

EXAMPLE 4

A trypsin and precipitation treatment similar to that described in Example 3 was performed for a group of brans or concentrates prepared from known varieties. The content of β-glucan was determined enzymatically from both the original samples and dry final preparations. The following results were obtained in the experiment:

| Cultivar variety | Origin | Pretreatment | β-glucan % | |
|---|---|---|---|---|
| | | | before | after treatment |
| Yty | Finland | Bran | 12.0 | 18.9 |
| Yty | Finland | Concentrate | 26.1 | 29.3 |
| Sang | Sweden | Concentrate | 19.7 | 20.8 |
| Mortlock | Australia | Bran | 7.5 | 11.1 |
| Salo | Finland | Bran | 12.2 | 16.9 |
| Virma | Finland | Bran | 11.7 | 16.0 |
| Nasta | Finland | Bran | 12.6 | 15.2 |

EXAMPLE 5

A concentrate prepared as described in Example 1 from the variety Yty was incubated as described in Example 2, but replacing trypsin with commercial enzymes of microbiological origin, and adjusting pH and incubation temperature to optimal values of each enzyme used. Using most of the enzymes, the viscosity of the suspension did not elevate, indicating that β-glucan was hydrolyzed. By hydrolysing using Esperase enzyme by Novo A/S, Brabrand, Denmark, the amount added being 0.30 mL/L, at pH 7.6 and 58° C. for two hours, an elevation of viscosity was achieved. To inactivate the protease and further solubilize β-glucan, the mixture was heated to 80° C. and incubated at this temperature during one hour. Soluble fibre was precipitated by adding 94% ethanol, 133% of the weight of the mixture, and the solids were separated and dried. After drying, the starch separated was removed by sieving. The yield of the dry fibre after sieving was 90% from the amount of the concentrate used as starting material. The same treatment was repeated with another batch without the enzymatic hydrolysis step. Viscosities of 2.5% suspensions in phosphate buffer pH 2.5 of the starting material and both of the treated batches were determined as function of extraction time at 37° C. and were the following (n.m.=not measurble):

|  | Starting material | | Viscosity mPa s Esperase, heating, precipitation | | Heating, precipitation | |
| --- | --- | --- | --- | --- | --- | --- |
| Shear rate | 43 s$^{-1}$ | 697 s$^{-1}$ | 43 s$^{-1}$ | 697 s$^{-1}$ | 43 s$^{-1}$ | 697 s$^{-1}$ |
| 10 min extr. | n.m. | 14 | 240 | 62 | n.m. | 28 |
| 20 min extr. | n.m. | 19 | 333 | 73 | 187 | 42 |
| 30 min extr. | n.m. | 23 | 390 | 77 | 248 | 49 |

EXAMPLE 6

Oat grains of cultivar variety Yty were dehulled and ground without being previously heat treated, using uncorrugated rollers. Subsequently the flakes were ground in a hammer mill, and the bran was separated as the coarse fraction using a sieve with openings of 125 μm. β-Glucan content of the bran was 9.5%.

250 g of the bran obtained was extracted and heat inactivated in respect of enzyme activities by treating in a 85% (weight per weight) mixture of ethanol and water at its boiling point during 2 hours. Subsequently, the mixture was screened using a sieve with openings of 71 μm, the coarse fraction was resuspended in ethanol and the wet screening repeated three times. The yield of the coarse fraction after the washing steps and drying was 77 g. 70 g of the bran concentrate thus obtained was suspended in 190 mL of 0.02M sodium phosphate buffer of pH 7.5, preheated to 40° C., and 0.175 g of trypsin was added. The mixture was kept at 40° C. for two hours, under which time it turned to a highly viscous paste. The paste was heated to 80° C. in a microwave oven, and kept at this temperature during one hour. In the hot mixture, 420 mL of 92% (weight per weight) ethanol was added, and the mixture blendend with a shearing mixer until homogenous. It was screened by using a sieve with openings of 71 μm, and washed on the screen three times. The yield of the coarse fraction after drying was 49.7 g, its β-glucan content 35.9%. β-Glucan content of the 49.7 g, its β-glucan content 35.9%. β-Glucan content of the fine fraction was 6.9%. In centrifugal treatments it could be separated to starch and dietary fibre fractions.

We claim:

1. A method for preparing a concentrate of soluble dietary fibre selected from the group consisting of β-glucan and pentosans, from a milled raw material derived from cereal grains, comprising the steps of:

inactivating said raw material in respect of β-glucanase and pentosanase enzymes;

adding water to said inactivated raw material to form a suspension;

heating said suspension to a temperature of 60–85 degrees celsius to extract soluble fibre from other cell wall components of said inactivated raw material so that a suspension of solid particles and soluble dietary fibre is obtained;

adding a polar organic solvent to said suspension so as to precipitate the extracted soluble dietary fibre onto said solid particles;

homogenizing said suspension to detach fine-granuled solids, from said particles containing said precipitated dietary fibre;

separating said fine-granuled solids on the basis of particle size and/or density from coarse particles containing said precipitated dietary fibres;

separating said coarse particles containing said precipitated dietary fibre from any liquid remaining from the suspension and drying said coarse particles containing said precipitated dietary fibre to form a final product.

2. A method according to claim 1 wherein said raw materials are derived from grains of oat, barley or rye.

3. A method according to claim 1, further comprising the step of:
   adding an amount of water, said amount being smaller than needed for gelatinization of said starch, wherein starch granules remain microscopically intact after heating.

4. A method according to claim 2, further comprising the step of:
   adding an amount of water, said amount being smaller than needed for gelatinization of said starch, wherein starch granules remain microscopically intact after heating.

5. A method according to claim 1, further comprising the step of:
   before said heating step, adding to said suspension a proteolytic enzyme which does not contain β-glucan or pentosan degrading activity at a pH of said suspension.

6. A method according to claim 2, further comprising the step of:
   before said heating step, adding to said suspension a proteolytic enzyme which does not contain β-glucan or pentosan degrading activity at a pH of said suspension.

7. A method according to claim 3, further comprising the step of:
   before said heating step, adding to said suspension a proteolytic enzyme which does not contain β-glucan or pentosan degrading activity at a pH of said suspension.

8. A method according to claim 4, further comprising the step of:
   before said heating step, adding to said suspension a proteolytic enzyme which does not contain β-glucan or pentosan degrading activity at a pH of said suspension.

9. A method according to claim 5, wherein said enzyme used is trypsin.

10. A method according to claim 6, wherein said enzyme used is trypsin.

11. A method according to claim 7, wherein said enzyme used is trypsin.

12. A method according to claim 8, wherein said enzyme used is trypsin.

13. A method according to claim 9, wherein said raw material is a cultivar variety where the viscosity of its β-glucan is elevated by a mild hydrosysis by trypsin.

14. A method according to claim 6, wherein said raw material is a cultivar variety where the viscosity of its β-glucan is elevated by a mild hydrosysis by trypsin.

15. A method according to claim 11, wherein said raw material is a cultivar variety where the viscosity of its β-glucan is elevated by a mild hydrosysis by trypsin.

16. A method according to claim 12, wherein said raw material is a cultivar variety where the viscosity of its β-glucan is elevated by a mild hydrosysis by trypsin.

17. A method according to claim 1, wherein said solvent precipitating said dietary fibre is ethanol.

18. A method according to claim 1, further comprising the step of:
    adding solid carrier particles on which the precipitation of dietary fibre occurs to the suspension.

19. A method according to claim 1, further comprising the step of:
    extracting lipids from said particles containing said dietary fibre before drying.

* * * * *